(12) United States Patent
Goff

(10) Patent No.: US 7,053,195 B1
(45) Date of Patent: May 30, 2006

(54) LOCKED NUCLEIC ACID CONTAINING HETEROPOLYMERS AND RELATED METHODS

(75) Inventor: Stephen A. Goff, Encinitas, CA (US)

(73) Assignee: Syngenta participatious AG, Basel (CH)

( * ) Notice: Subject to any disclaimer, the term of this patent is extended or adjusted under 35 U.S.C. 154(b) by 426 days.

(21) Appl. No.: 10/166,280

(22) Filed: Jun. 10, 2002

Related U.S. Application Data

(60) Provisional application No. 60/386,222, filed on Jun. 12, 2001.

(51) Int. Cl.
 *C07H 21/04* (2006.01)
(52) U.S. Cl. ............... 536/23.1; 536/24.3; 536/25.3
(58) Field of Classification Search ............... 536/23.1, 536/24.3, 25.3
 See application file for complete search history.

(56) References Cited

U.S. PATENT DOCUMENTS

| | | | |
|---|---|---|---|
| 5,212,295 A | 5/1993 | Cook | |
| 5,223,618 A | 6/1993 | Cook et al. | |
| 5,386,023 A | 1/1995 | Sanghvi et al. | |
| 5,489,677 A | 2/1996 | Sanghvi et al. | |
| 5,565,350 A | 10/1996 | Kmiec | |
| 5,731,181 A | 3/1998 | Kmiec | |
| 5,795,972 A | 8/1998 | Kmiec | |
| 2003/0051270 A1* | 3/2003 | Kmiec et al. | ................. 800/21 |

FOREIGN PATENT DOCUMENTS

| | | |
|---|---|---|
| WO | WO 92/20703 A1 | 11/1992 |
| WO | WO 95/14706 A1 | 6/1995 |
| WO | WO 99/14226 A2/3 | 3/1999 |

OTHER PUBLICATIONS

Capecchi, M.R., "Altering the genome by homologous recombination." *Science*, 244:1288-1292 (1989).
Caruthers, M.H., "Gene synthesis machines: DNA chemistry and its uses." *Science*, 230:281-285 (1985).
Chang, J. et al., "A sensitive new prenatal test for sickle-cell anemia." *N. Eng. J. Med.*, 307:30-32 (1982).
Cole-Strauss, A. et al., "Correction of the mutation responsible for sickle cell anemia by an RNA-DNA oligonucleotide." *Science*, 273:1386-1389 (1996).
Cormier, J. et al., "Synthesis of hexanucleotide analogues containing diisopropylsilyl internucleotide linkages." *Nucleic Acids Res.*, 16:4583-4594 (1988).
Eckstein, F., "Nucleoside phosphorothioates." *Ann. Rev. Biochem.*, 54:367-402 (1985).
Egholm, M. et al., "Peptide nucleic acids (PNA). Oligonucleotide analogues with an achiral peptide backbone." *J. Am. Chem. Soc.*, 114:1895-1897 (1992).

Froehler, B. et al., "Phosphoramidate analogues of DNA:sythesis and thermal stability of heteroduplexes." *Nucleic Acid Research*, 16(11):4831-4839 (1988).
Glemarec, C. et al., "Conformational studies of thymidine dimers containing sulfonate and sulfonamide linkages by NMR spectroscopy." *Tetrahedron*, 49(11):2287-2298 (1993).
Greever, R. et al., "Direct identification of sickle cell anemia by blot hybridization." *Proc. Natl. Acad. Sci.*, 78(8):5081-5085 (1981).
Huang, S. et al,. "Acyclic nucleic acid analogues:synthesis and oligomerization of γ,4-diamino-2-oxo-1(2H)-pyrimidinepentanoic acid . . ." *J. Org. Chem.*, 56:6007-6018 (1991).
Huang, Z. et al., "Building blocks for oligonucleotide analogues with dimethylene sulfide, sulfoxide, and sulfone groups replacing . . ." *J. Org. Chem.*, 56:3869 (1991).
Huie, E. et al., "Oligonucleotides with a nuclease-resistant sulfur-based linkage." *J. Org. Chem.*, 57:4569-4570 (1992).
Itakura, K., et al., "Synthesis and use of synthetic oligonucleotides." *Ann. Rev. Biochem.*, 53:323-356 (1984).
Jones, R. et al., "Synthesis and binding properties of pyrimidine oligodeoxynucleoside analogs containing neutral phosphodiester . . ." . *J. Org. Chem.*, 58:2983-2991 (1993).
Kren, B. et al, "In vivo site-directed mutagenesis of the factor IX gene by chimeric RNA/DNA oligonucleotides." *Nature Medicine* 4:285-290 (1998).
Miller, P. et al., "Control of ribonucleic acid function by oligonucleoside methylphosphonates." *Biochimie*, 67:769-776 (1985).
Ogilvie, K. et al., "Synthesis of a thymidine dinucleootide analogue containing an internucleotide silyl linkage." *Tetrahedron Letters*, 26(35):4159-4162 (1985).
Orkin, S. et al., "Improved detection of the sickle mutation by DNA analysis." *N. Eng. J. Med.*, 307:32-36 (1982).
Peffer, N. et al., "Strand-invasion of duplex DNA by peptide nucleic acid oligomers." *Proc. Natl. Acad. Sci. USA* 90:10648-10652 (1993).
Reynolds, R. et al., "Synthesis of thymidine dimers containing internucleoside sulfonate and sulfonamide linkages." *J. Org. Chem.*, 57:2983-2985 (1992).
Scaringe, S. et al., "Chemical synthesis of biologically active oligoribonucleotides using β-cyanoethyl protected . . ." *Nucleic Acids Research*, 18:5433-5441 (1990).

(Continued)

*Primary Examiner*—James Ketter
(74) *Attorney, Agent, or Firm*—Jenkins, Wilson, Taylor & Hunt, P.A.

(57) ABSTRACT

The present invention relates to methods of replacing nucleotides in target nucleic acid sequences using DNA-LNA chimeras. The method of the present invention provides for replacing a first nucleotide in a target sequence by exposing the target sequence to a DNA-LNA heteropolymer and thereby replacing the first nucleotide with a second nucleotide. The invention also features the DNA-LNA chimeras themselves as well as methods of making them.

52 Claims, 2 Drawing Sheets

OTHER PUBLICATIONS

Stirchak, E. et al., "Uncharged stereoregular nucleic acid analogues." *J. Org. Chem.*, 52:4202-4206 (1987).

Swiderski, P. et al, "Polystyrene reverse-phase ion-pair chromatography of chimeric ribozymes." *Anal. Biochem.*, 216:83-88 (1994).

Usman, N. et al., "Exploiting the chemical synthesis of RNA." *Trends Bioch. Sci.*, 17:334-339 (1992).

Usman, N. et al, "Large scale chemical synthesis, purification and crystallization of RNA-DNA chimeras." *Nucleic Acids Research*, 20:6695-6699 (1992).

Vasseur, J. et al., "Oligoncleosides: synthesis of a novel methylhydroxylamine,-linked nucleoside dimmer and its incorporation . . . " *J. Am. Chem. Soc.*, 114:4006-4007 (1992).

Wang, H. et al., "Solid phase synthesis of neutral oligonucleotide analogues." *Tetrahedron Letters* 32:7385-7388 (1991).

Wilson, J. et al., "Use of restriction endonucleases for mapping the allele for βs-globin." *Proc. Natl. Acad. Sci.*, 79:3628-3631 (1982).

Wosnick, M. et al., "Rapid construction of large synthetic genes:total chemical synthesis of two different versions of the bovine . . . " *Gene*, 60:115-127 (1987).

Yoon, K. et al., "Targeted gene correction of episomal DNA in mammalian cells mediated by a chimeric RNA-DNA oligonucleotide." *Proc. Natl. Sci. USA*, 93:2071-2076 (1996).

Zhu, T. et al., "Engineering herbicide-resistant maize using chimeric RNA/DNA oligonucleotides." *Nature Biotechnology*, 18:555-558 (2000).

Zhu, T. et al., "Targeted manipulation of maize genes in vivo using chimeric RNA/DNA oligonucleotides." *Proc. Natl. Acad. Sci.* 96:8768-8773 (1999).

Christensen, U. et al. Stopped-flow kinetics of locked nucleic acid (LNA)-oligonucleotide duplex formation: studies of LNA-DNA and DNA-DNA interactions. *Biochem.J.*, 354 (Pt3):481-484 (2001).

Jensen, G.A. et al. "A comparison of the solution structures of an LNA : DNA duplex and the unmodified DNA: DNA duplex." *Journal of the chemical society—Perkin Transactions 2*, 1224-1232 (2001).

Koshkin, A.A. et al. "LNA (Locked Nucleic Acids): Synthesis of the adenine, cytosine, guanin, 5-methylcytosine, thymine, and uracil bicyclonucleoside monomers, oligomerisation, and unprecedented nucleic acid recognition". *Tetrahedron*, 54:3607-3630 (1998).

Koshkin, A.A. et al. "LNA (Locked Nucleic Acid): An RNA mimic forming exceedingly stable LNA:LNA duplexes." *J. Am. Chem. Soc.*, 120:13252-13253 (1998).

Nielsen, K.E. et al. "Solution structure of an LNA hybridized to DNA: NMR study of the d(CT(L)GCT(L)T(L)CT(L)GC):d(GCAGAAGCAG) duplex containing four locked nucleotides." *Bioconjug Chem*, 11:228-238 (2000).

Nielsen, c.B. et al., "The solution structure of a locked nucleic acid(LNA) hybridized to DNA." *Journal of Biomoleculare Structure & Dynamics* 17(2):175-191 (1999).

Petersen, M. et al. "The conformations of locked nucleic acids (LNA)". *J. Mol. Recognit* . . 13:44-53(2000).

Singh, S.K. et al. "Universality of LNA-mediated high-affinity nucleic acid recognition". *Chem Commun*, 12:1247-1248 (1998).

Skouv, J and Jakobsen, M.H. "Locked Nucleic Acid (LNA): A new class of nucleic acid". *Pharmaceutical Mfg. Int'l.* 127-130 (Apr. 1999).

Wengel, J. et al, "LNA (Locked Nucleic Acid)." *Nucleosides & Nucleotides* 18(6&7):1365-1370 (1999).

* cited by examiner

```
          T
     5'-AC CTG ACT CCT GTG GAG AAG TCT GC-3'              β^S
        '' ''' '''
     3' TG GAC TGA GGA CAC CTC TTC AGA CG 5'

*

5'- AC CTG ACT CCT GAG GAG AAG TCT GC-3'             β^A

TG GAC TGA GGA CTC CTC TTC AGA CG

*

AI CTG ACT CCT GAG GAG AAG ACT GC                  δ

TA GAC TGA GGA CTC CTC TTC IGA CG

*

T GCGCG ug gac uga ggA CTC Cuc uuc aga cg T           SC1
  T                                           T        β^S → β^A
  T CGCGC AC CTG ACT CCT GAG GAG AAG TCT GC T
          3' 5'

T GCGCG ug gac uga ggA CAC Cuc uuc aga cg T           SC2
  T                                           T        β^A → β^S
  T CGCGC AC CTG ACT CCT GTG GAG AAG TCT GC T
          3' 5'

T GCGCG ua gac uga ggA CTC Cuc uuc uga cg T           SC3
  T                                           T     3 MISMATCHES TO
  T CGCGC AT CTG ACT CCT GAG GAG AAG ACT GC T              β^S
          3' 5'

T GCGCG ug gac uga ggA CTC Cuc uuc uga cg T           SC4
  T                                           T     2 MISMATCHES TO
  T CGCGC AC CTG ACT CCT GAG GAG AAG ACT GC T              β^S
          3' 5'

T CGCGC ac cug acu ccT GTG Gag aag ucu gc T           SC5
  T                                           T    TARGETS THE NON-
  T GCGCG TG GAC TGA GGA CAC CTC TTC AGA CG T        TEMPLATE STRAND OF
          5' 3'                                            β^A
```

FIG. 2

LOCKED NUCLEIC ACID CONTAINING HETEROPOLYMERS AND RELATED METHODS

RELATED APPLICATIONS

This application claims priority to U.S. Provisional Application serial number 60/386,222 filed Jun. 12, 2001, arising from conversion of non-provisional U.S. patent application Ser. No. 09/879,310, (entitled LOCKED NUCLEIC ACID CONTAINING HETEROPOLYMERS AND RELATED METHODS, and filed on Jun. 12, 2001), to a provisional application by petition filed in the U.S. Patent and Trademark Office on May 8, 2002, the specification of which in herein incorporated by reference in its entirety for all purposes.

FIELD OF THE INVENTION

The present invention relates to the fields of nucleic acid chimeras and methods of making single base changes in nucleic acid sequences. More particularly, the present invention relates to methods of using DNA-LNA (locked nucleic acid) heteropolymers to make single nucleotide base changes in target nucleic acid.

BACKGROUND OF THE INVENTION

Methods of changing one or more nucleotides in a nucleic acid sequence are useful in several applications, including the identification and alteration of gene function in an organism. Such site-directed gene manipulation has been moderately successful via homologous recombination in animal models, and particularly, in mammalian cell cultures. See, e.g., Yoon, et al., *Proc. Natl. Acad. Sci. USA*, 93:2071–2076 (1996).

Unfortunately, the success of conventional homologous recombination in animal models has been limited in plant cells due to the low frequency of homologous recombination. See, Zhu et al., *Proc. Natl. Acad. Sci.* 96:8768–8773 (1999). Moreover, this method also suffers from complications of random insertion in the absence of correct sequence homology. See, Capecchi, M. R., *Science* 244:1288–1292 (1989). Triple-helix forming oligonucleotides coupled to cross linking agents have been used with limited success to alter DNA sequences. However, the utility of this approach is constrained by the absolute necessity that the target DNA sequence must consist of homopyrimidine or homopurine stretches in the target DNA sequences.

Another method for gene targeting involves the use of chimeric DNA/RNA oligonucleotides to introduce single-point mutations in certain nucleotide sequences. Such mutations induced by chimeric DNA/RNA oligonucleotides generally have involved alteration of 1–2 base pairs in the target site, and is suitable for many applications, such as site specific mutagenesis, gene knockouts, and allelic replacements. For example, tyrosinase is an essential enzyme in melanin synthesis, produced by melanocytes, and sufficient for pigmentation change in vitro and in vivo. Melanocytes from albino mice contain a homozygous point mutation (T GT→TCT) in the tyrosinase gene. This results in an amino acid sequence change from Cys to Ser at amino acid 85 of the mature tryosinase. This single amino acid change is responsible for the complete inactivation of tyrosinase and the resultant absence of pigmentation. Thus, correction of the point mutation in tyrosinase gene results in the restoration of the enzyme activity and in changes of the pigmentation of the cell.

This ability to correct single point mutations has enabled the creation of therapeutic strategies for the treatment of genetic diseases not otherwise available. For example, sickle cell anemia is the classic prototype of a hereditary hemoglobinpathy resulting from a point mutation in the β-globin gene. The single point correction of an A- to -T mutation within the β-globin results in the change from a mutant valine to the normal glutamic acid residue. Correction of the mutant allele through a gene conversion mechanism provides a means for gene therapy that avoids the the attendant problems associated with current therapies such as transduction methods based on retro- and adenovirus vectors. See, e.g., Cole-Strauss, et al. *Science*, 273:1386–1389 (1996).

It may be possible to use such chimeric DNA/RNA oligonucleotides to: (1) create cell and animal disease models for drug target validation (2) produce novel plants with desired input traits, e.g., heat, cold and salt resistance, and output traits, e.g., higher fiber content and nutritional value (3) correct small genetic mutations that cause disease (4) alter normal genes and thereby modulate disease-relevant pathways and (5) optimize other industrial applications such as fermentation. See, http://www.valigen.net/tech.htm.

Chimeric mutational vectors (CMVs) having non-natural nucleotides are described in U.S. Pat. Nos. 5,731,181 and 5,795,972. The CMVs are said to comprise two complimentary oligoncleobase strands, wherein the oligonucleobases are either ribo-type (i.e., having a 2' hydroxyl) or 2'-deoxyribo-type. At least three contiguous bases of one strand are ribo-type nucleobases, preferably nuclease resistant nucleobases. The patents state that the nucleobases of a chain of a CMV can be any nucleobase now known or to be developed that hybridizes by Watson-Crick base pairing to DNA. CMVs have been shown to effect single point mutations in wild type human liver/bone/kidney episomal alkaline phosphatase.

While these strategies have been successful in animal models, little is known about the use of single point gene modification or the introduction of CMVs in plant systems. As noted above, the applicability of site-specific gene modification has wide reaching utilities in the agricultural industry, including the development of herbicide- and disease-resistant plants. For such applications, heritablity of gene modifications and stable transmission of modified genetic traits to plant progeny is a necessity. While chimeric DNA/RNA oligonucleotides have been used to engineer herbicide-resistant maize plants without integrating foreign genes or regulatory sequences into the plants, the frequency rates in plants are approximately three orders of magnitude lower than those reported for chimeric gene modification in animal systems. See, Zhu et al., *Nature Biotechnology*, 18:555–558 (2000). Studies suggest this lower success rate may be due to the differences in efficiencies of homologous pairing, strand transfer, or mismatch repair between mammalian and plant cells. Thus, a need remains for addressing these lower frequencies of gene modification in plant systems. Likewise, there exists a need to improve upon the homologous pairing, strand transfer, or mismatch repair efficiencies currently attainable.

Even in animal models, the success rate of current chimeric RNA-DNA techniques converting single point mutations is quite low, hovering around 13–30%. See generally, Kren et al, *Nature Medicine* 4:285–290 (1998). Indeed, the low frequency of specificity remains a serious limitation in the realm of therapeutics. Severe difficulties arise under conditions where the single point mutation is inaccessible due to intrastrand folding and intermolecular conformational stabilities.

Recently, oligonucleotide analogues have been developed to investigate the conformational transition that occurs when oligonucleotides hybridize to a target sequence, from the relatively random coil structure of the single stranded state to the ordered structure of the duplex state. For example, conformationally restricted oligonucleotide analogues that include locked nucleoside analogues (LNAs) are described in PCT WO 99/14226. As an example, bicyclic LNAs contain nucleosides with a 2'-O-4'-C methylene bridge. Other bicyclic and tricyclic LNAs are described therein and are incorporated by reference, including any drawings. This conformational and steric hindrance is believed to inhibit nuclease attack of the LNAs, thereby resulting in an increased thermal stability of duplexes formed between LNAs and complementary DNA or RNA. To date, while LNAs have been developed as blocking agents for translation and transcription in vitro and in vivo, as sequence specific inhibitors such as PCR clamping, as well as in various antisense therapies, the unique capabilities of LNA have not been harnessed for use in the repair of single point mutations. See. e.g., www.proligo.com.

Thus, there still remains a need for additional methods of replacing nucleotides in target nucleic acid sequences for a wide variety of uses relating to the identification and alteration of gene function in an organism. Accordingly, a need also exists for an improved method of introducing a single point mutation into cells with an increased efficiency than is currently attainable.

SUMMARY OF THE INVENTION

The present invention relates to methods of replacing nucleotides in target nucleic acid sequences using DNA-LNA heteropolymers. In one embodiment, a first nucleotide is exposed to LNA-DNA heteropolymer and the target nucleotide replaced with a second nucleotide. The invention also features the DNA-LNA heteropolymers themselves as well as methods of making them.

In the present disclosure, "heteropolymers" refer to polymers of non-identical subunits, which are linked by oriented phosphodiester bonds or their derivatives, into polymers.

In the present disclosure, an "oligonucleotide" has its usual term in molecular biology. It refers to a polymer of nucleobases that can hybridize by Watson-Crick base pairing to a complementary sequence.

In the present disclosure, nucleobases comprise a base, which is purine, pyrimidine, or a derivative or analog thereof. Nucleobases include peptide nucleobases, the subunits of peptide nucleic acids, and morpholine nuclebases as well as nucleosides, nucleotoids, and nucleotides. Nucleosides are nucleobases that contain a pentosefuranosyl moiety, e.g., an optionally substituted riboside or 2'deoxyriboside, and have a linkage to other nucleobases that does not contain a phosphorus. Nulceotoids are pentosefuranosyl containing nucleobases having linkages that contain pohosphorus, e.g., phosphorothioates, phosphoramidates and methylphosphonates, but not phosphates. nucleotides are pentosefuranosyl containing nucleobases that are linked by phosphodiesters. Nucelobases are either deoxyribo-type, ribo-type, or LNA type. Ribo-type nucleobases are pentosefuranozyl containing nucleobases wherein the 2' carbon is a methylene substituted with a hydroxyl, alkyloxy or halogen moiety. Deoxyribo-type nucleobases are nucleobases other than ribo-type and LNA-type nucleobases and include all nucleobases that do not contain a pentosefuranosyl moiety. LNA-type nucleobases are nucleobase analogues of either ribo-type or deoxyribo-type nucleobases that contain either bicyclic or tricyclic alkyl- or alkylene bridges, as described in PCT WO 99/14226.

References herein to a "portion" of a DNA or RNA chain, or of a gene, mean a linear chain that has a nucleotide sequence which is the same as a sequential subset of the sequence of the chain to which the portion refers.

In the present disclosure, the term "complementary" has its usual meaning from molecular biology. Two nucleotide sequences or strands are complementary if they have sequences which would allow base pairing (Watson-Crick or Hoogsteen) according to the usual pairing rules. This does not require that the strands would necessarily base pair at every nucleotide; two sequences can still be complementary with a low level (e.g., about 1–3%) of base mismatch such as that created by deletion, addition, or substitution of one or a few (e.g., up to 5 in a linear chain of 25 bases) nucleotides, or a combination of such changes.

In the present disclosure, "hybridize" has its usual meaning from molecular biology. It refers to the formation of a base-paired interaction between nucleotide polymers. The presence of base pairing implies that a fraction of the nucleotides (e.g., at least 80%) in each of two nucleotide sequences are complementary to the other according to the usual base pairing rules. The exact fraction of the nucleotides which must be complementary in order to obtain stable hybridization will vary with a number of factors, including nucleotide sequence, salt concentration of the solution, temperature, and pH.

In the present disclosure, "duplex" has its usual meaning in molecular biology and refers to strands of nucleic acids wherein each base of a first strand of the duplex corresponds to a base of a second strand of the duplex according to the scheme in which uracil or thymine and adenine correspond and cytosine and guanine correspond. Anti-parallel duplex strands having these correspondences are said to be Watson-Crick paired. Duplex nucleic acids can be of two major types, ribonucleic acids and deoxyribonucleic acids. Each ribonucleotide has an equivalent deoxyribonucleotide, e.g., adenosine and deoxyadenosine, cytidine and deoxycytidine, guanosine and deoxyguanosine, uridine and thymidine.

References herein to the term "correspond," as in, for example, cDNA which "corresponds" to mRNA, means that at least a portion of one nucleic acid molecule is either complementary or homologous to a second nucleic acid molecule. Thus, a cDNA molecule may correspond to the mRNA molecule where the mRNA molecule was used as a template for reverse transcription to produce the cDNA molecule. Similarly, a genomic sequence of a gene may correspond to a cDNA sequence where portions of the genomic sequence are homologous or complementary to the cDNA sequence.

References herein to the statement that bases are "Watson-Crick paired" or that they form a "duplex nucleic acid" is to be understood to mean that under the proper conditions of temperature and salt they are capable of forming base pairs or a duplex nucleic acid. It is understood that under some conditions of low salt and/or elevated temperature, the Watson-Crick base pairs may cease to be thermodynamically stable such that the duplex nucleic acid denatures.

In one aspect, the invention provides a method of replacing a first nucleotide in a target nucleic acid sequence. The method involves the step of exposing the target nucleic acid sequence to a DNA-LNA heteropolymer and thereby replacing the first nucleotide with a second nucleotide.

In preferred embodiments, the first and/or second nucleotides are independently selected from the group consisting of adenine, thymine, uracil, cytosine, guanine, deoxyadenosine, deoxycytidine, deoxyguanosine, uridine, and thymidine. The target nucleic acid sequence preferably is in or from an organism, for example a monocot or dicot plant such as maize or tobacco or an animal such as a mammal. The target nucleic acid sequence may be a DNA template that consist of deoxyribonucleotides or an RNA template that consists of ribonucleotides. Examples of target nucleic acid sequences are a gene encoding AHAS, an episomal target nucleic acid sequence, a chromosomal target nucleic acid sequence, an endogenous gene, a transgene, a recessive gene, and a dominant gene.

In another aspect, the present invention provides a DNA-LNA heteropolymer. The DNA-LNA heteropolymer includes a strand of DNA linked to a strand of LNA. The invention also provides a method of making a DNA-LNA heteropolymer. The method involves the step of linking a DNA to a LNA.

Because LNAs may be derivatives of any nucleobase, the limitations placed on triplex affinity capture, namely the necessity of homopurine or homopyrimidine rich residues in the target sequence, are absent from the present invention. Advantageously, DNA-LNA heteropolymers may selectively isolate and bind with a wide diversity of nucleotidic sequences, unhampered by base limitations. For example, the present invention is capable of site-specific nucleotidic recognition from nucleotide sequences composed of heteropurinic or heteropyrimidinic bases that are currently not detectable using a triplex affinity capture method.

LNAs form more stable duplexes than their DNA or RNA counterparts. As such, the present invention imparts distinct advantages over the current art. The ability of LNAs to form stable duplexes with their target nucleotide sequence under conditions, such as low ionic strength or in buffers containing strong chaotropic agents, i.e., conditions in which RNA-DNA or DNA—DNA duplexes are unattainable, manifests itself in LNAs' increased hybridization affinities for target nucleic acid sequences. Thus, the disadvantages of unphysiological pH and ionic strength conditions suffered by triplex affinity capture methods are eliminated in the present invention. The enhanced stability of LNAs is particularly beneficial when isolating a single base pair and identifying single point mutations. Generally, DNA—DNA duplexes require high ionic strength conditions in order to form stable duplexes. By contrast, LNA-DNA duplexes form stable duplexes at much lower ionic strength (salt) conditions. Higher ionic strength conditions induce intrastrand folding of target DNA or RNA sequences. The ability to form stable duplexes at decreased salt concentrations decreases intrastrand folding and thereby increases the probability of exposing the targeted mutation or base pair(s). Because of the extreme sequence specificity needed to identify or isolate a single base pair, accessibility of the target strand is essential.

As another advantage related to the accessibility of target sequences, LNA sequences are particularly useful where the target sequence is difficult or impossible to access by unmodified oligonucleotide sequences due to the rapid formation of stable intramolecular structures such as those occurring in rRNA, tRNA, snRNA, and scRNA. LNAs present a distinct advantage over unmodified oligonucleotides in that the steric bulkiness and rigidity of the bicyclic component of LNAs hinder such intramolecular folding, thereby increasing the accessibility and exposure to single point mutations of 1–2 base pair sequences.

Because of the enhanced stability and thus, affinity, of LNA complexes, single mismatches in LNA duplexes cause considerable drops in thermal stability and result in LNA duplexes' heightened ability to discriminate single base pair differences compared to conventional RNA-DNA or DNA—DNA duplexes. Heightened discrimination between single base pair differences is of paramount importance when isolating a single point mutation and the sequence specificity of 1 or 2 base pairs.

As a further advantage, LNA sequences capture target sequences via strand displacement in which the LNA sequence selectively binds to its complementary target sequence in double stranded DNA or RNA such that the second strand of the double strand is displaced. See, e.g., PCT WO 99/14226. Unlike colony or plaque hybridization, which frequently require prior denaturation steps, the present invention is able to detect and isolate intact double stranded DNA. The strand displacement mechanism of the present invention also obviates the labor intensive, multistep washing procedures required of colony and plaque hybridization techniques.

The method described in the present invention may be used, without limitation, to improve a crop, in a reverse genetics method, and/or to confer a new property or trait on an organism, such as herbicide resistance to an imidazoline. The method preferably produces site-specific mutagenesis, a gene knockout or an allele replacement. The method may be performed in vitro or in vivo and preferably it stablely transmits a modified trait through mitosis and meiosis to progeny. The method may also involve the steps of synthesizing and purifying the DNA-LNA heteropolymer and/or growing cells to maturity.

In another aspect, the present invention features a method of replacing a first nucleotide in a target nucleic acid sequence in one or more of a plurality of cells. The method involves the step of exposing said plurality of cells to one or more DNA-LNA heteropolymers and thereby replacing said first nucleotide with a second nucleotide in at least one or more of the plurality of cells.

While certain aspects of the invention have been summarized herein, other useful applications, embodiments, and aspects of the invention are disclosed in the detailed description and in the drawings.

BRIEF DESCRIPTION OF THE DRAWINGS

These and other features and advantages of the present invention will be appreciated from the following detailed description, along with the accompanying figure in which like reference numerals identify like elements throughout and wherein:

FIG. 2 shows sequences of codons 309 and adjacent dinucleotides of codons 2 and 10 of $\beta^S$-globin, $\beta^A$-globin, and DNA-LNA heteropolymers SC 1–SC5.

DETAILED DESCRIPTION OF THE INVENTION

Figure 1:
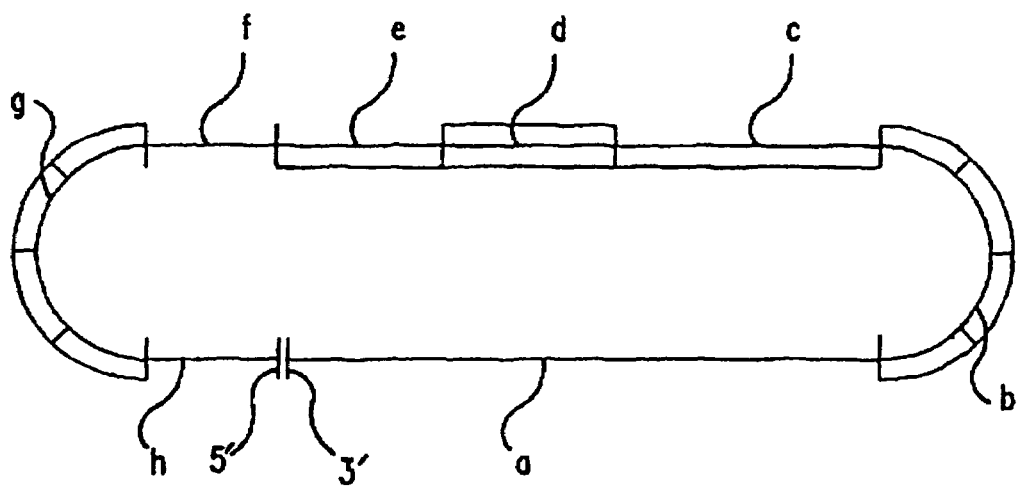
FIG. 1 shows a general form of one embodiment of a DNA-LNA heteropolymer.

The present invention provides for compounds, termed DNA-LNA heteropolymers, that can be used to make specific changes in the genome of a eukaryotic cell. The DNA-LNA heteropolymers of the present invention may be in the form of any duplex of nucleic acids such as duplex nucleic acids, chimeric nucleic acids, heteroduplex nucleic acids, hairpin duplex nucleic acids, and/or homo-duplex nucleic acids. For definitions, see U.S. Pat. Nos. 5,565,350, and 5,792,972 incorporated herein by reference in their entirety, including any drawings.

The DNA-LNA heteropolymers of the present invention include a DNA strand and a LNA strand and optionally may include a linker. The sequence of the DNA strand and the LNA strand consists of at least two regions that are homologous to the target gene and one or more regions ("mutator regions") that differ from the target gene and introduce the genetic change into the target gene. The mutator region is directly adjacent to homologous regions in both the 3' and 5' directions. In a preferred embodiment, each mutator region is adjacent in both the 3' and the 5' directions to homologous regions of at least three bases. In another preferred embodiment, each mutator region is flanked in both the 3' and 5' directions by LNA nucleobase segments of at least three bases, which segments need not be adjacent to the mutator region. The flanking LNA nucleobase segments need not be directly adjacent to the mutator region, i.e., a portion of the homologous region comprising DNA type nucleobases can intervene. The total length of all homologous regions is preferably at least 14 bases. If the heteropolymer contains two homologous regions separated by a mutator region, the homologous regions can more preferably be each between 8 and 12 bases long and most preferably be 10 bases long.

At least two homologous regions of the LNA strand are comprised of at least three contiguous LNA-type nucleobases which are Watson-Crick paired to deoxyribo-type nucleobases of the second strand. In a preferred embodiment, there are between 9 and 25 LNA-type nucleobases and more preferably 20 LNA-type nucleobases in the first strand, which are Watson-Crick paired to deoxyribo-type nucleobases of the second strand. According to the invention, a region of homo-duplex nucleic acids can be disposed between the hybrid-duplex/homologous regions of DNA-LNA heteropolymer. The interposed homo-duplex can contain the heterologous region. When the heterologous region is less than about 50 base pairs and preferably less than about 20 base pairs, an interposed homo-duplex that contains the heterologous region is preferred.

In one embodiment, there are no LNA-type nucleobases in the second strand. DNA-LNA heteropolymer is further characterized by containing at least three nuclease resistant LNA-type nucleobases. In a preferred embodiment, all LNA-type nucleobases are nuclease resistant.

The mutator region can be as large as 2 kilobases (kb) and can encode an exon. preferably the mutator region consists of 20 or fewer bases, more preferably 6 or fewer bases and most preferably 3 or fewer bases. The mutator region can be of a length different than the length of the sequence that separates the regions of the target gene homologous with the homologous regions of the heteropolymer so that an insertion or deletion of the target sequence or base results. In another embodiment, the mutator region of the first strand consists of deoxyribo-type nucleobases and is flanked by deoxyribo-type nucleobases. Alternatively, the mutator region can be comprised of LNA-type type nucleobases of the first strand and deoxyribo-type nucleobases of the second strand. When DNA-LNA heteropolymer is used to introduce a deletion, there is no base identifiable as within the mutator region. Rather, the mutation is effected by the juxtaposition of the two homologous regions that are separated in the target gene. In one embodiment, the mutator region is a deletion of from 6 to 1 bases or more preferably from 3 to 1 bases. Multiple separated mutations can be introduced by a single DNA-LNA heteropolymer, in which case there are multiple mutator regions in the same heteropolymer. Alternatively, multiple DNA-LNA heteropolymers can be used simultaneously to introduce multiple genetic changes in a single gene, or alternatively, to introduce genetic changes in multiple genes of the same cell.

I. Structure of Exemplary DNA-LNA Heteropolymers

DNA-LNA heteropolymers must contain at least one region of between at least 1 base and more usually 3 or 4 bases that are not Watson-Crick paired. These regions serve as linkers between the two strands of Watson-Crick paired bases. In contrast to other chimeric nucleotides that have been synthesized having regions of unpaired nucleotides, these heteropolymers have no enzymatic activity, i.e., they do not catalyze chemical reactions or themselves undergo chemical reaction in the absence of a biological energy source such as ATP. The bases of the linkers in the preferred embodiment are deoxyribonucleotides.

DNA-LNA heteropolymer having two linkers can be constructed so that the 3' and 5' ends of the polymer are Watson-Crick paired to adjacent nucleotides of the complementary strand. They are readily ligated, wherein DNA-LNA heteropolymer forms a single continuous circular nucleic acid polymer. Substantially all the remaining bases of the DNA-LNA heteropolymer are Watson-Crick paired.

a. Single Chain DNA-LNA Heteropolymers

In one embodiment, DNA-LNA heteropolymer is a single 5'3'-linked oligonucleotide chain comprising between about 40 and about 100 nucleobases. A single chain DNA-LNA heteropolymer can contain unpaired nucleotides, which form one or two hairpin turns, which turn or turns divide(s) the DNA-LNA heteropolymer into the first and second strands, so that at least 15 bases of the first strand can be Watson-Crick paired to bases of the second strand.

FIG. 1 shows the structure of one embodiment of a single chain DNA-LNA heteropolymer with segments (a)–(h). In the embodiment of FIG. 1, the first strand consists of segments (c), (d) and (e), which is complementary to a second strand consisting of segment (a). In this particular embodiment, the 3' terminus of the DNA-LNA heteropolymer is illustrated to be at the 3' end of the (a) segment and the 5' terminus is shown to be at the 5' end of the (h) segment. However, the location of the termini and the orientation of 3' and 5' directions of the DNA-LNA heteropolymer with respect to the segments can be elsewhere, so long as the termini do not interrupt the homologous or mutator regions of the first or second strands. The segments are labeled sequentially (a) through (h).

In one embodiment, the lengths and characteristics of the segments are as follows. Segment (a) ranges between 16 and 40 nucleotides and preferably between 20 and 30 nucleotides. The sequence of the region of segment (a) can be either that of the coding strand or the non-coding strand of the gene that contains the intended mutation (the "mutated target gene"). The location of the sequence of segment (a) must include the portion of the target gene that is to be changed. Unless the target gene is not normally transcribed in target cell, preferably the sequence of segment (a) is the sequence of the coding strand of the target gene. When the target gene is not transcribed in the target cell, neither the coding strand sequence or the non-coding strand sequence is preferred. The sequence of segment (a) determines the sequences and combined lengths of segments (c)–(e), which must be complementary to segment (a).

The oligonucleobases of the portion of segment (a) that are base paired with segments (c) and (e) can be any 2'-deoxyribo-type nucleobases. The nucleobases of segments (c) and (e), which are termed LNA-type nucleobase segments, can be any LNA type nucleobase that is known or will be developed. In a preferred embodiment, the nucleotides of segment (d), which is termed the intervening segment are 2'-deoxyribo-type nucleobases. Alternatively, segment (d) can be made of LNA-type nucleobases; in which case the boundaries between segments (c), (d) and (e) are not defined. Segments (b) and (f) through (h) can be of any type of nucleobase.

In a preferred embodiment, the sequence of segments (c) and (e) are completely homologous to the target sequence. However, a one base mutator region in the (c) or (e) segment can result in the mutation of the target gene at the homologous position. For example, the nucleotide to be modified may be adenine, thymine, cytosine, guanine uraal, deoxyadenosine, deoxycytidine, deoxyguanosine, uridine, or thymidine.

Segments (b) and (g) are about 4 nucleotides in length and form single stranded hairpin turns that allow segments (a) and (c)–(e) and segments (f) and (h) to form Watson-Crick base pairs, i.e., to form duplex nucleic acids. In alternative embodiments the function of segments (b) and (c), which is to covalently link the first and second strands, can be served by non-oligonucleobase moieties. Segments (c) and (e), also termed the first and second LNA-type segments, consist, in one embodiment, of LNA nucleotides containing a 2'O-4'-C methylene bridge. In a preferred embodiment, segments (c) and (e) are independently, between 6 and 13 nucleotides.

Segment (d), also termed the intervening segment, in one embodiment, is between 4 and 20 nucleotides in length. If the target gene contains two or more point mutations that are separated by fewer than 15 nucleotides, each can be repaired by the same DNA-LNA heteropolymer.

Segments (f) and (h) form a duplex that brings the 3' and 5' ends of the DNA-LNA heteropolymer, which is nicked between segments (a) and (h) into juxtaposition. The structure formed by segments (f), (g) and (h) is termed a hairpin cap. A hairpin cap contains a terminal end and a nonterminal end. The terminal end forms a terminus of the chain, which can be either a 5' or a 3' terminus. The function of a hairpin cap is to control the position of the 3' or 5' terminus. The non-terminal end of the hairpin cap can be ligated to an end of a strand, whereby the end of the complementary strand, which is the second terminus of the chain is juxtaposed to the terminal end of the hairpin cap, as shown in FIG. 1. The 3' and 5' termini can be, in one embodiment, dephosphorylated. In an alternative embodiment, the 3' and 5' termini can be covalently linked by a phosphodiester bond or equivalent, wherein the DNA-LNA heteropolymer is a closed circular oligonucleotide. Segments (f) and (h) can be optionally deleted from a closed circular DNA-LNA heteropolymer. In a preferred embodiment, the orientation of the oligonucleobase of the hairpin cap is the same as the orientation of the strand to which it is linked. If the orientation of the hairpin cap is anti-parallel to the orientation of the strand to which it is attached, the designation as 3' or 5' of the terminal end of the hairpin is determined by the structure of terminal end of the complementary.

In a preferred embodiment, the DNA-LNA heteropolymer is a single chain DNA-LNA heteropolymer containing one hairpin cap, oriented in parallel with the chain, having juxtaposed 3' and 5' ends. There are eight specific embodiments of this type, which are defined by the location of the ligation between the hairpin cap and the chain and by whether the sequence of the first strand is the sequence of the coding strand or the non-coding strand of the target gene. Eight representative species are given in Table I. FIG. 1 illustrates species 2 and 6 of Table I.

TABLE I

| Species | Location of ligation of Hairpin Cap and Chain | Sequence of First Strand |
|---|---|---|
| 1 | 3' First Strand | Coding |
| 2 | 5' First Strand | Coding |
| 3 | 3' Second Strand | Coding |
| 4 | 5' Second Strand | Coding |
| 5 | 3' First Strand | Non-coding |
| 6 | 5' First Strand | Non-coding |
| 7 | 3' Second Strand | Non-coding |
| 8 | 5' Second Strand | Non-coding |

DNA-LNA heteropolymers having a homo-duplex region interposed between two hybrid-duplex regions can be constructed using semisynthetic techniques. Two synthetic chimeric polynucleic acids having a hairpin conformation are to be constructed. The free 5' and 3' ends of the two chimeric nucleic acids are constructed with an overlap staggered ends complementary to the overlap of two different restriction enzyme digest products. A homo-duplex region is provided having the complementary restriction enzyme digested ends. The addition of a restriction enzyme sites to the ends of a cloned DNA fragment can be accomplished by techniques well understood by those skilled in the art, e.g., without limitation, PCR amplification with extended primers of the blund end ligation of linkers containing the restriction site. The two chimeric nucleotides and the homo-duplex region can be ligated by conventional enzymatic techniques. The product, having chimeric oligonucleotides ligated at both ends can be separated from the incompletely reacted substrates by electrophoresis in 6% polyacrylamide gel in Tris Borate EDTA buffer under non-denaturing conditions. The linear capped molecules are constrained and are electrophoresced more slowly under these conditions.

b. Dual Chain DNA-LNA Heteropolymers

The DNA-LNA heteropolymers of the present invention may be produced generally as described in Zhu et al., Nature Biotechnology, 18:555–558 (2000) and Zhu et al., Proc. Natl. Acad. Sci. 96:8768–8773 (1999), both of which are incorporated herein by reference in their entirety, including any drawings. LNA starting materials may be obtained commercially from Proligo or may be produced generally as described in International Patent Application Publication No. WO 99/14226.

Alternatively, the DNA-LNA heteropolymers can also comprise two chains, each chain having a 3' and a 5' terminus, wherein a first comprises the first strand and a second chain comprises a second strand. The first strand comprises LNA molecules complementary to the first sequence of the target nucleic acid sequence except for a single nucleotide on the first strand at a position corresponding to the position of the nucleotide to be modified on the target sequence. The second strand comprises a sequence of deoxyribonucleic acids completely complementary to the first strand. In one embodiment, the first strand is about 10–100 nucleic acids long. In another embodiment, the second strand is about 10–100 nucleic acids long.

In one embodiment, DNA and LNA residues are completely complementary to the target sequence except for a single non-complementary nucleotide corresponding to the position of the nucleotide to be modified.

The nucleotide to be modified may be adenine, thymine, cytosine, guamine, uracil, deoxyadenosine, deoxycytidine, deoxyguanosine, uridine or thymidine.

Similarly, the single non-complementary nucleotide may be adenine, thymine, cytosine, guanine, uracil, deoxyadenosine, deoxycytidine, deoxyguanosine, uridine, or thymidine.

The first and second chains can be cross-linked by a covalent linker or the first and second chains can be held in association only by Watson-Crick bases pairing. The lengths of the regions and segments of the first and second strands of a two chain DNA-LNA heteropolymer are constructed according to the foregoing guides regarding single chain DNA-LNA heteropolymer. In one embodiment, the first and second chains can further comprise complementary segments of between 3 and 10 bases that flank the first and second strands that increase the stability of the association between the first and second chains.

An alternative embodiment of two chain DNA-LNA heteropolymers comprises a double hairpin structure, namely, two oligonucleobase chains and two hairpin caps; the first strand is a part of the first chain and the second strand is a part of the second chain. The hairpin caps can both be ligated to the ends of one strand. In one specific configuration, termed a "cradle" configuration, a hairpin cap is ligated to each end of the second strand. In an "anti-cradle" configuration, the hairpin caps are ligated to the ends of the first strand. An alternative type of configuration, termed "head-to-tail," consists of a hairpin cap ligated to each of the strands. Because the strands of the DNA-LNA heteropolymer hybridize only in an antiparallel fashion, there are only two specific configurations of the head-to-tail type: the hairpin caps can both be ligated to either the 3' ends or the 5' ends of the strands.

Those skilled in the art are aware of a wide variety of DNAs, LNAs and linkers that may be used in the present invention. For example, in a preferred embodiment, suitable LNAs are described in International Patent Application Publication No. WO 99/14226.

II. Synthesis of DNA-LNA Heteropolymers and Selection of Nucleobases

DNA-LNA heteropolymers of the present invention can be synthesized and purified by any method. For example, they may be synthesized by modification of the techniques used in the solid phase synthesis of DNA. Reviewed, Caruthers, M. H., *Science*, 230:281–285 (1985); Itakura, K., et al., *Ann. Rev. Biochem.*, 53:523–56 (1984). Modifications to permit synthesis of chimeric nucleic acids are disclosed in Scarainge, S. A., e al., *Nucleic Acids Research*, 18:5433–41 (1990); Usman, N., et al, *Nucleic Acids Research*, 20:6695–99 (1992); and Swiderski, P. M., et al, *Anal. Biochem.*, 216:83–88 (1994), which are hereby incorporated by reference in their entirety, including any drawings. Recent advances concerning the synthesis of chimeric nucleic acids are reviewed in Usman, N. & Cedergren, R., *Trends Bioch. Sci.*, 17:334–9 (1992).

LNA nucleobase sequences may be obtained commercially from Proligo, LLC (Boulder, Colo.). Alternatively, LNA oligonucleobase sequences may be synthesized according to the methods described in PCT WO 99/14226, or by any other methods know to those skilled in the art of synthesizing modified oligonucleotide sequences.

For DNA-LNA having chains up to about 100 bases in length, the preferred technique is solid-phase synthesis. Alternatively, subsegments of DNA-LNA chains greater than about 50 bases in length can be synthesized by solid phase synthesis and ligated by liquid phases techniques, well known to those skilled in the art. Wosnick, M. A., *Gene*, 60:115–117 (1987). As those skilled in the art appreciate, complementary subsegments can be synthesized by solid-phase techniques so that when annealed, the ends of the subsegments are staggered. By causing adjacent subsegments to have complementary staggered ends, adjacent segments can be ligated by well known enzymatic processes. By this technique a chain of a DNA-LNA heteropolymers considerably larger than 100 bases can be synthesized.

The nucleobases of a chain of a DNA-LNA heteropolymers can be any nucleobase now known or to be developed that hybridizes by Watson-Crick base pairing to DNA. Suitable nucleobases include nucleotides and nucleotoids. The structure and synthesis of oligonucleobases having exemplary nucleotoids can be found as follows: Phosphorothioates, Eckstein, F., *Ann. Rev. Biochem.*, 54:367 (1985); Phosphoramidates, Froehler, B. C., et al., *Nucleic Acid Research*, 16:4831 (1988); Methylphosphonates, Miller, P. S., et al., *Biochimie*, 67:769 (1985). A method of producing oligonucleotoids having chiral-specific phosphorus-containing linkages is described in U.S. Pat. No. 5,212,295. Chirally-specific oligonucleotides having the appropriately selected isomer hybridize to DNA with improved stability.

Pentosefuranosyl containing nucleobases that are linked by non-phosphorus nucleobases that can be used as deoxyribo-type nucleobases, which are termed nucleosides. Nucleosides that form duplexes with DNA that are at least as stable as DNA/DNA duplexes are linked by the various linkage chemistries known in the art. Typical chemistries and methods for their use in oligonucleobases are described as follows: methylhydroxylamine linkages, Vasseur et al., *J. Am. Chem. Soc.*, 114:4006 (1992), U.S. Pat. Nos. 5,386,023 and 5,489,677; alkylene dioxy linkages, U.S. Pat. No. 5,223,618; and 3'-Thioformacetal, Jones et al., *J. Org. Chem.*, 58:2983 (1993).

Other representative nucleosides that can be used in DNA-LNA include: Carbamates, Stirchak et el., *J. Org. Chem.*, 52:4202 (1987); Sulfonate & Sulfonamide, Glemarec et al., *Tetrahedron*, 49:2287 (1993); Reynolds et al., *J. Org. Chem.*, 57:2983 (1992); Sulfone, Huang, Z., *J. Org. Chem.*, 56:3869 (1991); Sulfamate, Huie, E. M., et al., *J. Org. Chem.*, 57:4569 (1992); and Diisopropylsilyl & silyl, Cormier and Ogilvie, *Nucleic Acids Res.*, 16:4583 (1988); Ogilvie & Cormier, *Tetrahedron Lett.*, 26:4159 (1985).

Nucleobases that lack a pentosefuranosyl moiety can be used as deoxyribo-type nucleobases. Suitable examples include replacement of the pentosefuranosyl phosphate moiety by a Morpholino carbamate, Wang & Weller, *Tetrahedron Lett.*, 32:7385 (1991) and peptide nucleic acids in which the pentosefuranosyl phosphate moiety is replaced by an aminoethylglycine. Peptide nucleic acids (PNA) are described in Egholm et al., *J. Am. Chem. Soc.*, 114:1895 (1992) and Huang, B. S. et al., *J. Org. Chem.*, 56:5006 (1991) and WO 92/20703 to Buchardt et al.; methods of making PBA/oligonucleotide chimeric polymers is described in WO 95/14706.

Those skilled in the art understand that PNA can hybridize to DNA in either orientation, i.e., either end of a PNA can be the 3' or 5' end. Peffer, N. J., et al., 1993, Proc. Natl. Acad. Sci. 90:10648–52. When a peptide nucleobase is present in an oligonucleobase strand having pentosefuranosyl-containing nucleobases, the 3' and 5' ends of the strand are determined by the orientation of the pentosefuranosyl moieties or, if none are present in the chain having the peptide nucleobase, then the 3' and 5' ends of the strand are determined by the orientation of pentosefuranosyl nucleobases of the complementary strand. Note, that the first strand of a DNA-LNA heteropolymers must contain at least three pentosefuranosyl nucleobases.

III. The Use of the DNA-LNA Heteropolymers of the Invention

The present invention also provides for a method of introducing changes into a known nucleotide sequence using DNA-LNA heteropolymers. For example, the DNA-LNA heteropolymers of the present invention can be used to introduce a mutation in a specific location in the genome of a target cell. The target cell may be from any plant or animal organism. For example, the plant may be without limitation a monocot or a dicot, maize or tobacco. The organism may be an animal, such as a mammal. The specific location of the target location is defined by its nucleic sequence hereinafter referred to as the target sequence. For example, the target nucleic acid sequence may be a DNA or RNA template, a gene encoding AHAS, an episomal or chromosomal target nucleic acid sequence, an endogenous gene, a transgene, a recessive gene or a dominant gene.

The change can result in the replacement of one or more nucleotides or can be an insertion or deletion or one or more nucleotides. In preferred embodiments the replacement, insertion or deletion can be of 20 or fewer contiguous bases. In a more preferred embodiment, the replacement, insertion or deletion can be of 6 or fewer bases and most preferably of 3 or fewer bases. The insertion can be as long as about two kilobases. The insertions or deletions can be made in the coding and the regulatory parts of the gene.

According to the invention, DNA-LNA heteropolymers are constructed wherein the homology regions are identical to the target sequence, except for the presence of some regions of hybrid-duplex. The change to be introduced is encoded by the heterologous region. When the change in the target sequence is the addition of less than about 20 bases, the invention may be practiced using one or two regions of hybrid duplex. When the change in the target sequence is the addition of more than about 50 bases it is preferred that the heterologous region be contained within a homo-duplex region.

The method of the present invention provides for replacing a first nucleotide in a target sequence by exposing the target sequence to a DNA-LNA heteropolymer and thereby replacing said first nucleotide with a second nucleotide. The first nucleotide may be adenine, thymine, cytosine, guanine, uracil, deoxyadenosine, deoxycytidine, deoxyguanosine, uridine or thymidine. The second nucleotide may be adenine, thymine, cytosine, guanine, uracil, deoxyadenosine, deoxycytidine, deoxyguanosine, uridine, or thymidine.

The practice of the invention requires that the DNA-LNA heteropolymer be introduced into the nucleus of the target cell. Any method which causes such introduction can be used. For example, lipifection, particle bombardment, electroporation, DEAE-dextran, calcium phosphate precipitation, liposome mediated fusion (LIPOFECTIN), direction injection or any other method of transfection may be used.

In one embodiment, the transfection is performed with liposomal transfer compound, e.g., DOTAP (n-[1-2,3,dioleoyloxypropyl]-N,N,N,-trimethylammonium methylsulfate, Boehringer-Mannhaeim) or an equivalent, such as LIPOFECTIN. The amount of DNA-LNA heteropolymer is not critical to the practice of the invention; good results can be acieved with 10 nM/$10^5$ cells. A ratio of about 500 ng of DNA-LNA heteropolymer in 3 μg of DOTAP per $10^5$ cells can be used. In one embodiment, transfection techniques can be used with the modification that the transfected cells are cultured in serum free media, media supplemented with human serum albumin, or human serum.

In another embodiment, DNA-LNA heteropolymer may be used to construct transgenic animals. The DNA-LNA heteropolymer introduced into the pronucleus of an ovum by direct injection, according to the method described in Brinster, R. L., et al, *Proc. Natl. Acad. Sci.* 86:7087 (1989); see also U.S. Pat. No. 4,973,191, which are hereby incorporated by reference herein in their entirety, including any drawings. Alternatively, the DNA-LNA heteropolymers can be introduced into an embryonic stem cell, chimeric animals can be produced by aggregation of the embryonic stem cell within normal blastocyst cells, and transgenic animals can be recovered as offspring of the chimeric animals, according to the method of Capecchi, *Science,* 244:1288 (1989), which is hereby incorporated by reference in its entirety, including any drawings.

Using electroporation, as many as 1 cell per 10,000 treated cells can be specifically mutated at the target sequence (hereinafter "transformed"). The practice of the invention, thus, includes the use of a method to select the transformed cells from among the larger number of unmutated cells. In one embodiment, the transformation of cells confers a growth advantage. Non-limiting examples of such growth advantages include drug-resistance, alterations in growth regulation, and alteration in the capacity to utilize metabolites. In an alternative embodiment, the method of selection can be negative selection whereby the transformed cells are rendered incapable of growth under the selecting conditions in the non-transformed cells are removed by exposure to conditions that selectively destroy proliferating cells. When the method of introducing DNA-LNA heteropolymers into the cell is direct injection, as for example, when constructing transgenic animals by pronuclear injection, the rate of transformation can be greater than 1 per 10,000 cells. The need for selection is thereby considerably reduced. Alternatively the transformed cells may have an altered cell-surface antigenic phenotype that can be detected by immunofluorescence and selection can be performed by a Fluoresecence Activated Cell Sorter.

The present method may also be used to repair mutations in genetic diseases such as Gaucher Disease, thalassemia, Sickle Cell disease, or any other disease identified by site-specific mutagenesis. The present invention may also be used to improve a crop, confer herbicide resistance (e.g., resistance to imidazoline), or confer new phenotypes, properties, or traits to plants as well as animals. Other applications include the introduction of stop codons or frame shift mutations to make gene "knock-outs", i.e., transgenic animals or plants that lack a functional copy of a specific gene, as well as transgenic animals or plants having specific mutations. In a still further method of use encompassed by the present invention, specific mutations can be made for the purpose of studying the structure function relationships of genes-of-interest, or to produce allele replacements. Advantageously, when a desirable mutation has been identified in one species, it can be introduce in the homologous genes of other species by use of the present invention. This method may be performed in vitro or in vivo. For example, this method stably transmits a modified trait through mitosis and meiosis to progeny.

For medical purposes, the invention can be used to repair mutations or introduce mutations into any cell-type that can be removed from a subject's body, cultured and reimplanted into the subject. Techniques for the removal, culture and reimplantation of hepatocytes, in particular of hepatic reserve (stem) cells, have been described in patent publication WO 94/08598. Examples of genetic diseases that can be cured by repair of mutations in hepatocytes include: familial hypercholesteremia, caused by mutation in the LDL receptor; emphysema caused by a mutation in the α1-antitrypsin gene; and hemophilia and Christmas Disease, which are caused by mutations in coagulation factors VIII and IX, respectively.

In yet a further use of the method, DNA-LNA heteropolymer may be used to mutagenize a population of cells wherein a mutant having a selectable phenotype can be obtained. According to this aspect of the invention, a mixture of DNA-LNA heteropolymers having a mutator region of one or several nucleotides is synthesized such that three non-wild type nucleotides are present at each position of the mutator region. The treatment of a population of cells with such a mixture of DNA-LNA heteropolymers will induce a variety of mutations in the target gene. After an appropriate selection step, a mutant having the desired phenotype can be recovered.

In this method of the present invention, the DNA-LNA heteropolymer may be DNA-LNA duplex nucleic acid, LNA chimeric nucleic acid, LNA heteroduplex nucleic acid, DNA-LNA hairpin duplex nucleic acid, or DNA-LNA homo-duplex nucleic acid.

a. The Use of DNA-LNA to Mutate the b-Globin Gene in EBV-Transformed Cell Lines

A DNA-LNA heteropolymer may be employed to repair the mutation found in Sickle Cell Disease b-globin, FIG. 2. For example, DNA-LNA heteropolymer composed of DNA residues with two intervening blocks of ten LNA residues flanking a short stretch of five DNA residues may be used. When the heteropolymer folds into the duplex conformation, one strand contains only DNA residues while the other strand contains the LNA/DNA blocks. In one embodiment, the internal sequence is complementary to the $b^s$ globin sequence over a stretch of 25 residues that span the site of the $b^s$ mutation, with the exception of a single base (T) which is in bold and designated with an asterisk. The five DNA residues flanked by LNA residues were centered about the mutant T residue in the $b^s$ coding sequence. A control chimeric oligonucleotide (SC2) was designed in the same manner with the exception of the base (A) designated in bold and with an asterisk. Genomic sequences of the $b^A$, $b^S$, and closely-related b-globin genes are also displayed in FIG. 2 with the specific site of $b^s$ mutation printed in bold.

Lymphoblastoid cells may be prepared as follows. Heparin-treated blood may be obtained from discarded clinical material of a patient with sickle cell disease and from a source with neither history nor symptoms of the disease. Mononuclear cells may be prepared from blood (~8 ml) by density gradient centrifugation in Ficoll and infected with Epstein-Barr virus which has been propagated in the marmoset cell line B95-8 (Coriell Institute for Medical Research #GM07404D). Infections may be performed with addition of 0.1 mg leucoagglutinin PHA-L in 10 ml RPMI medium supplemented with 20% fetal bovine serum in a T25 flask. Cultures are fed twice a week starting on day 5 and are considered established once 60–70% of the cells remains viable at day 21. The $b^A$ and $b^s$ lymphoblastoid cells may be maintained in RPMI medium containing 10% fetal bovine serum.

The DNA-LNA heteropolymer is introduced into the above-described lymphoblastoid cells homozygous for the $b^s$ allele as follows. Cells (1×10⁵ per ml) are seeded in 1 ml of medium in each well of a 24-well tissue culture plate the day prior to the experiment. Transfections may be performed by mixing chimeric oligonucleotides with 3 mg of DOTAP (N-1-(2,3-Dioleoyloxy)propyl-N,N,N-trimethylammonium methylsulfate, Boehringer-Mannheim) in 20 ml of 20 mM HEPES, pH 7.3, incubating at room temperature for 15 min, and added to the cultured cells. After 6 h the cells may be harvested by centrifugation, washed and prepared for PCR amplification following the procedure of E. S. Kawasaki, PCR Protocols, Eds. M. A. Innis, D. H. Gelfand, J. J. Sninsky and T. J. White, pp146–152, Academic Press, (1990).

Correction of the single base mutation may be assessed by taking advantage of well known restriction fragment length polymorphisms resulting from the $b^s$ mutation, R. F. Greeves et al., Proc. Natl. Acad. Sci., 78:5081 (1981); J. C. Chang and Y. W. Kan, N. Eng. J. Med., 307:30 (1982); S. H. Orkin et al., ibid., p. 32; J. T. Wilson et al., Proc. Natl. Acad. Sci., 79:3628 (1982). The A to T transversion in the $b^s$ allele results in the loss of a Bsu36I restriction site (CCTGAGG). Thus, the $b^s$ allele can be detected by Southern hybridization analysis of genomic DNA cut with Bsu36I. A 1.2 kbp Bsu36I DNA fragment of the b-globin gene present normally is absent in the $b^s$ allele and is replaced by a diagnostic 1.4 kbp fragment. When genomic DNA recovered from homozygous $b^s$ lymphoblastoid cells is analyzed by this procedure, the expected 1.4 kbp fragment should be observed.

To measure the efficiency of correction rapidly and sensitively, a PCR-based RFLP analysis may be adapted. For the analysis of the b-globin sequence, the 345 bp PCR fragment is prepared by amplification from a crude cell lysate using primers BG02 (5'-TCCTAAGCCAGTGCCA-GAAGA-3' (SEQ ID NO:9)) and BG05 (5'-CTATTG-GTCTCCTTAAACCTG-3' (SEQ ID NO:10)) and Expand Taq polymerase (Boehringer Mannheim). For the analysis of the b-globin gene, the same cell extracts used in amplification reactions with primers DG06 (5'-CTCACAAACTAAT-GAAACCCTGC-3' (SEQ ID NO:11)) and DG07 (5'-GAAAACAGCCCAAGGGACAG-3' (SEQ ID NO:12)) may be used to generate a 335 bp fragment. Gels may be stained with SYBR™ green (FMC Bioproducts) and fluorescence intensities may be quantitated using a Molecular Dynamics fluoroimager. DNA sequencing may be performed in both directions using an ABI 373A sequencer.

The above primers are designed to yield a 345 bp fragment spanning the site of the $b^s$ mutation after PCR amplification of genomic DNA. The fragment from normal cells contains a Bsu36I recognition sequence and yields fragments of 228 bp and 117 bp, while DNA from $b^s$ gene contains the sequence CCTGTGG and remains refractory to cutting. Analysis will indicate that the 345 bp DNA fragment amplified from SC1-treated $b^s$ cells is partially cleaved with Bsu36I, indicating correction of the mutation on some, but not all, chromosomes. A quantitative measure may be obtained by comparing the relative intensities of the three DNA fragments after electrophoretic separation and staining with the fluorescent dye SYBR™ green. The stained bands may be imaged using a laser fluoroimager and the relative levels calculated. Conversion efficiency is quantitated by scanning the cyber green-stained agarose gel with a fluoroimager.

The specificity of the action of DNA-LNA heteropolymers may be assessed by sequencing the related b-globin gene, which is more than 90% homologous to the b-globin gene. The band bglobin genes are identical over the 5 bp DNA core targeting region of SC1. Two single base differences are underlined in FIG. 2. To determine whether SC2 altered the b-globin gene, DNA sequence analysis may be performed as above. The results showed that no alteration was introduced into the b-globin gene by the SC2 DNA-LNA in contrast to the observed change directed by SC2 in the $b^A$-globin sequence.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description are also within the scope of the present invention and that preferred embodiments or features of one aspect of the invention can be incorporated into any of the other aspects of the present invention.

What is claimed is:

1. A heteropolymer for introducing a single base change in a target oligonucleotide, wherein the target oligonucleotide comprises a 3' → 5' strand of contiguous nucleic acids having a target sequence of nucleic acids comprising a nucleotide to be modified, wherein said heteropolymer comprises:
a first strand having a sequence of nucleic acids that is completely complementary to the target sequence of nucleic acids except for a single nucleotide on the first strand at a position corresponding to the position of the nucleotide to be modified on the target sequence, wherein the first strand comprises one or more locked nucleic acids;
and a second strand having a sequence of deoxyribonucleic acids that is completely complementary to the first strand,
wherein at least two homologous regions of the first strand comprise at least 3 contiguous LNA-type nucleobases which are Watson-Crick paired to deoxyribo-type nucleobases of the second strand.

2. A heteropolymer of claim 1, wherein the first strand comprises deoxyribonucleic acid and locked nucleic acid residues that are completely complementary to the target sequence of nucleic acids except for a single non-complementary nucleotide corresponding to the position of the nucleotide to be modified.

3. A heteropolymer of claim 2, wherein the deoxyribonucleic acid residues of the first strand comprise the single non-complementary nucleotide corresponding to the position of the nucleotide to be modified and the nucleotides adjacent to the corresponding nucleotide.

4. A heteropolymer of claim 2, wherein the deoxyribonucleic acid residues are contiguous to one another and wherein the locked nucleic acids are directly positioned on either side of the deoxyribonucleic acid residues of the target sequence of nucleic acids.

5. A heteropolymer of claim 1, wherein the first strand is between about 10 and about 100 nucleic acids long.

6. A heteropolymer of claim 1, wherein the second strand is between about 10 and about 100 nucleic acids long.

7. A heteropolymer of claim 1, wherein the first stand and second strand are linked in a double hairpin structure.

8. A heteropolymer of claim 1, wherein the nucleotide to be modified is adenine.

9. A heteropolymer of claim 1, wherein the nucleotide to be modified is thymine.

10. A heteropolymer of claim 1, wherein the nucleotide to be modified is cytosine.

11. A heteropolymer of claim 1, wherein the nucleotide to be modified is guanine.

12. A heteropolymer of claim 1, wherein the nucleotide to be modified is uracil.

13. A heteropolymer of claim 1, wherein the nucleotide to be modified is deoxyadenosine.

14. A heteropolymer of claim 1, wherein the nucleotide to be modified is deoxyctyidine.

15. A heteropolymer of claim 1, wherein the nucleotide to be modified is deoxyguanosine.

16. A heteropolymer of claim 1, wherein the nucleotide to be modified is uridine.

17. A heteropolymer of claim 1, wherein the nucleotide to be modified is thymidine.

18. A heteropolymer of claim 1, wherein the single non-complementary nucleotide is adenine.

19. A heteropolymer of claim 1, wherein the single non-complementary nucleotide is thymine.

20. A heteropolymer of claim 1, wherein the single non-complementary nucleotide is cytosine.

21. A heteropolymer of claim 1, wherein the single non-complementary nucleotide is guanine.

22. A heteropolymer of claim 1, wherein the single non-complementary nucleotide is uracil.

23. A heteropolymer of claim 1, wherein the single non-complementary nucleotide is deoxyadenosine.

24. A heteropolymer of claim 1, wherein the single non-complementary nucleotide is deoxycytidine.

25. A heteropolymer of claim 1, wherein the single non-complementary nucleotide is deoxyguanosine.

26. A heteropolymer of claim 1, wherein the single non-complementary nucleotide is uridine.

27. A heteropolymer of claim 1, wherein the single non-complementary nucleotide is thymidine.

28. The heteropolymer of claim 1, wherein the target oligonucleotide is in or from an organism.

29. The heteropolymer of claim 28, wherein the organism is a plant.

30. The heteropolymer of claim 29, wherein the plant is maize.

31. The heteropolymer of claim 29, wherein the plant is a monocot.

32. The heteropolymer of claim 29, wherein the plant is a dicot.

33. The heteropolymer of claim 29, wherein the plant is tobacco.

34. The heteropolymer of claim 28, wherein the organism is an animal.

35. The heteropolymer of claim 34, wherein the animal is a mammal.

36. The heteropolymer of claim 1, wherein the target oligonucleotide is a DNA template that consist of deoxyribonucleotides.

37. The heteropolymer of claim 1, wherein the target oligonucleotide is an RNA template that consists of ribonucleotides.

38. The heteropolymer of claim 1, wherein the target oligonucleotide is a gene encoding AHAS.

39. The heteropolymer of claim 1, wherein the target oligonucleotide is an episomal target nucleic acid sequence.

40. The heteropolymer of claim 1, wherein the target oligonucleotide is a chromosomal target nucleic acid sequence.

41. The heteropolymer of claim 1, wherein the target oligonucleotide is an endogenous gene.

42. The heteropolymer of claim 1, wherein the target oligonucleotide is a transgene.

43. The heteropolymer of claim 1, wherein the target oligonucleotide is a recessive gene.

44. The heteropolymer of claim 1, wherein the target oligonucleotide is a dominant gene.

45. The heteropolymer of claim 1, wherein the heteropolymer is in vivo.

46. The heteropolymer of claim 1, wherein the heteropolymer is in vitro.

47. The heteropolymer of claim 1, wherein said heteropolymer is a DNA-LNA duplex nucleic acid.

48. The heteropolymer of claim 1, wherein said heteropolymer is a DNA-LNA chimeric nucleic acid.

49. The heteropolymer of claim 1, wherein said heteropolymer is a DNA-LNA heteroduplex nucleic acid.

50. The heteropolymer of claim 1, wherein said heteropolymer is a DNA-LNA homo-duplex nucleic acid.

51. The heteropolymer of claim 1, wherein said heteropolymer is a DNA-LNA homo-duplex nucleic acid.

52. A method of making a heteropolymer of claim 1, comprising the step of linking the first strand to the second strand or the step of synthesizing a chain of nucleic acids that takes the from of the heteropolymer comprising the first strand and the second strand.

* * * * *

```
                              SEQUENCE LISTING

<160> NUMBER OF SEQ ID NOS: 12

<210> SEQ ID NO 1
    <211> LENGTH: 25
    <212> TYPE: DNA
    <213> ORGANISM: Homo sapiens

<400> SEQUENCE: 1
acctgactcc tgtggagaag tctgc                                             25

<210> SEQ ID NO 2
    <211> LENGTH: 25
    <212> TYPE: DNA
    <213> ORGANISM: Homo sapiens

<400> SEQUENCE: 2
acctgactcc tgaggagaag tctgc                                             25

<210> SEQ ID NO 3
    <211> LENGTH: 25
    <212> TYPE: DNA
    <213> ORGANISM: Homo sapiens

<400> SEQUENCE: 3
atctgactcc tgaggagaag actgc                                             25

<210> SEQ ID NO 4
    <211> LENGTH: 68
    <212> TYPE: DNA
    <213> ORGANISM: Artificial Sequence
    <220> FEATURE:
    <223> OTHER INFORMATION: DNA-LNA Heteropolymer composed of DNA residues
          with two intervening blocks of ten LNA residues flanking a short
          stretch of DNA residues at position 40 to 44.

<400> SEQUENCE: 4
acctgactcc tgaggagaag tctgcttttg cagacuucuc ctcaggaguc aggugcgcgt       60
```

```
tttcgcgc                                                              68

<210> SEQ ID NO 5
<211> LENGTH: 68
<212> TYPE: DNA
<213> ORGANISM: Artificial Sequence
<220> FEATURE:
<223> OTHER INFORMATION: DNA-LNA Heteropolymer composed of DNA residues
      with two intervening blocks of ten LNA residues flanking a short
      stretch of DNA residues at position 40 to 44.

<400> SEQUENCE: 5
acctgactcc tgtggagaag tctgcttttg cagacuucuc cacaggaguc aggugcgcgt    60
tttcgcgc                                                              68

<210> SEQ ID NO 6
<211> LENGTH: 68
<212> TYPE: DNA
<213> ORGANISM: Artificial Sequence
<220> FEATURE:
<223> OTHER INFORMATION: DNA-LNA Heteropolymer composed of DNA residues
      with two intervening blocks of ten LNA residues flanking a short
      stretch of DNA residues at position 40 to 44.

<400> SEQUENCE: 6
atctgactcc tgaggagaag actgcttttg cagucuucuc ctcaggaguc agaugcgcgt    60
tttcgcgc                                                              68

<210> SEQ ID NO 7
<211> LENGTH: 68
<212> TYPE: DNA
<213> ORGANISM: Artificial Sequence
<220> FEATURE:
<223> OTHER INFORMATION: DNA-LNA Heteropolymer composed of DNA residues
      with two intervening blocks of ten LNA residues flanking a short
      stretch of DNA residues at position 40 to 44.

<400> SEQUENCE: 7
acctgactcc tgaggagaag actgcttttg cagucuucuc ctcaggaguc aggugcgcgt    60
tttcgcgc                                                              68

<210> SEQ ID NO 8
<211> LENGTH: 68
<212> TYPE: DNA
<213> ORGANISM: Artificial Sequence
<220> FEATURE:
<223> OTHER INFORMATION: DNA-LNA Heteropolymer composed of DNA residues
      with two intervening blocks of ten LNA residues flanking a short
      stretch of DNA residues at 25 to 29.

<400> SEQUENCE: 8
gcgcgttttc gcgcaccuga cucctgtgga gaagucugct tttgcagact tctccacagg    60
agtcaggt                                                              68

<210> SEQ ID NO 9
<211> LENGTH: 21
<212> TYPE: DNA
<213> ORGANISM: Artificial Sequence
<220> FEATURE:
<223> OTHER INFORMATION: Primer BG02

<400> SEQUENCE: 9
tcctaagcca gtgccagaag a                                               21
```

-continued

```
<210> SEQ ID NO 10
<211> LENGTH: 21
<212> TYPE: DNA
<213> ORGANISM: Artificial Sequence
<220> FEATURE:
<223> OTHER INFORMATION: Primer BG05

<400> SEQUENCE: 10
ctattggtct ccttaaacct g                                        21

<210> SEQ ID NO 11
<211> LENGTH: 23
<212> TYPE: DNA
<213> ORGANISM: Artificial Sequence
<220> FEATURE:
<223> OTHER INFORMATION: Primer DG06

<400> SEQUENCE: 11
ctcacaaact aatgaaaccc tgc                                      23

<210> SEQ ID NO 12
<211> LENGTH: 20
<212> TYPE: DNA
<213> ORGANISM: Artificial Sequence
<220> FEATURE:
<223> OTHER INFORMATION: Primer DG07

<400> SEQUENCE: 12
gaaaacagcc caagggacag                                          20
```